US009138306B2

(12) United States Patent
Guerra

(10) Patent No.: US 9,138,306 B2
(45) Date of Patent: Sep. 22, 2015

(54) DETACHMENT MECHANISM FOR A CENTRAL VENOUS ACCESS FILTER AND METHOD OF USE

(71) Applicant: BiO2 Medical, Inc., San Antonio, CA (US)

(72) Inventor: Rogelio Ivan Guerra, Lakewood, CO (US)

(73) Assignee: BIO2 MEDICAL, INC., Golden, CO (US)

( * ) Notice: Subject to any disclaimer, the term of this patent is extended or adjusted under 35 U.S.C. 154(b) by 129 days.

(21) Appl. No.: 13/918,861

(22) Filed: Jun. 14, 2013

(65) Prior Publication Data

US 2014/0005716 A1    Jan. 2, 2014

Related U.S. Application Data

(63) Continuation of application No. 13/292,942, filed on Nov. 9, 2011.

(51) Int. Cl.
*A61M 29/00* (2006.01)
*A61F 2/01* (2006.01)

(52) U.S. Cl.
CPC ............. *A61F 2/01* (2013.01); *A61F 2002/011* (2013.01); *A61F 2002/016* (2013.01); *A61F 2220/0033* (2013.01); *A61F 2220/0083* (2013.01); *A61F 2230/0067* (2013.01);
(Continued)

(58) Field of Classification Search
CPC ................ A61F 2/01; A61F 2002/011; A61F 2002/016; A61F 2230/0067

USPC .......................................... 606/108, 159, 200
See application file for complete search history.

(56) References Cited

U.S. PATENT DOCUMENTS

| 6,468,291 | B2 | 10/2002 | Bates et al. | 606/200 |
| 6,652,556 | B1 * | 11/2003 | VanTassel et al. | 606/200 |
| 7,144,408 | B2 | 12/2006 | Keegan et al. | 606/200 |

(Continued)

FOREIGN PATENT DOCUMENTS

| AM | WO 2012/088346 | 6/2012 | ............ A61M 29/02 |
| EP | 1733702 | 12/2006 | |

(Continued)

OTHER PUBLICATIONS

Decousus, et al., "A clinical trial of vena caval filters in the prevention of pulmonary embolism in patients with proximal deep-vein thrombosis", New Englad Journal of Medicine, vol. 338(7), pp. 409-415, (1998).

(Continued)

*Primary Examiner* — Victor Nguyen
(74) *Attorney, Agent, or Firm* — David G. Rosenbaum; J. Peter Paredes; Rosenbaum IP, P.C.

(57) ABSTRACT

A detachment and retrieval mechanism for a central venous access filter includes a catheter body, and an outer sheath concentrically disposed about the catheter body. The outer sheath and the catheter body are moveable relative to one another. A filter member includes a first end coupled to the catheter body and a second end movable relative to the catheter body. The first end may have a collar that is immovably coupled to the catheter body in a first state and movably coupled to the catheter body upon transition to a second state.

8 Claims, 10 Drawing Sheets

(52) U.S. Cl.
CPC .. *A61F 2230/0093* (2013.01); *A61F 2250/001* (2013.01); *A61F 2250/0039* (2013.01)

(56) References Cited

U.S. PATENT DOCUMENTS

| | | | |
|---|---|---|---|
| 2003/0130680 A1 | 7/2003 | Russell | 606/200 |
| 2003/0204168 A1* | 10/2003 | Bosma et al. | 604/103.02 |
| 2009/0062840 A1 | 3/2009 | Angel | 606/200 |
| 2010/0217304 A1 | 8/2010 | Angel et al. | 606/200 |
| 2010/0286722 A1 | 11/2010 | Rizk et al. | 606/200 |
| 2012/0016346 A1 | 1/2012 | Steinmetz et al. | 604/535 |

FOREIGN PATENT DOCUMENTS

| | | | |
|---|---|---|---|
| WO | WO 99/44542 | 9/1999 | A61F 2/06 |
| WO | WO 03/011185 | 2/2003 | A61F 2/00 |
| WO | WO 2006/031648 | 3/2006 | A61M 29/00 |
| WO | WO 2006-033958 | 3/2006 | |
| WO | WO 2011/068924 | 6/2011 | A61F 2/06 |

OTHER PUBLICATIONS

Lin, et al., "Vena Caval Filters in the Treatment of Acute DVT", Endovascular Today, pp. 40-50, (Jan. 2005).

International Preliminary Report on Patentability issued in corresponding foreign application, PCT/US2012/064371, pp. 1-6 (May 22, 2014).

European Search Report issued in corresponding foreign application, pp. 1-9 (May 28, 2015).

* cited by examiner

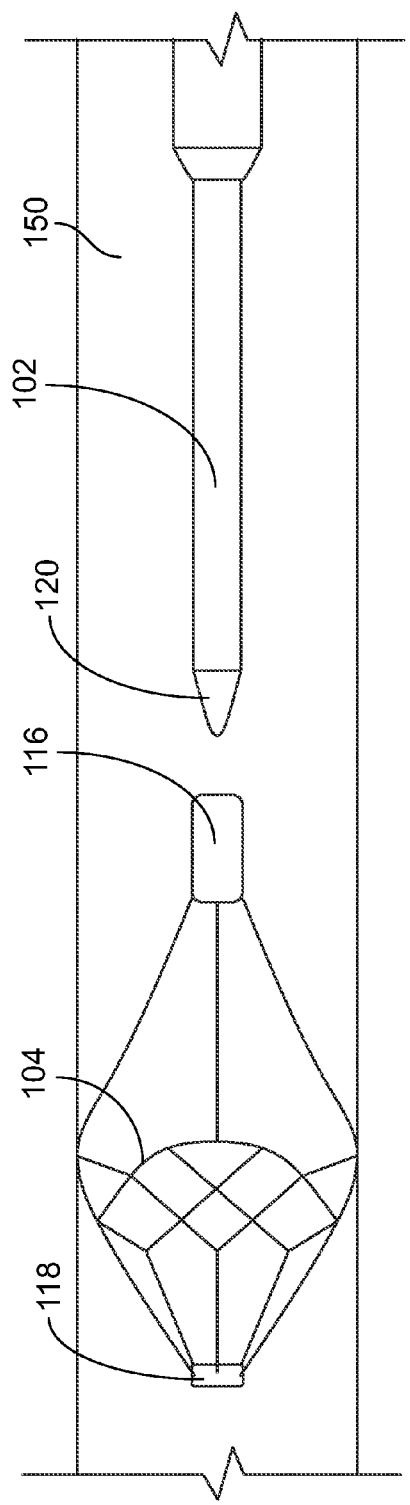
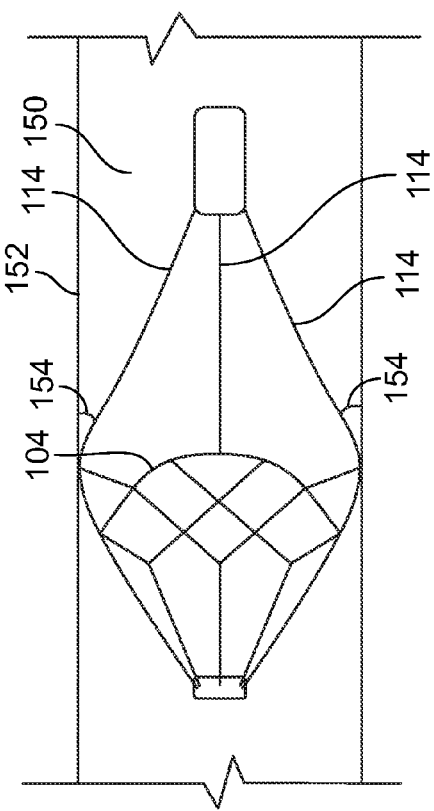
FIG. 8C
FIG. 8D

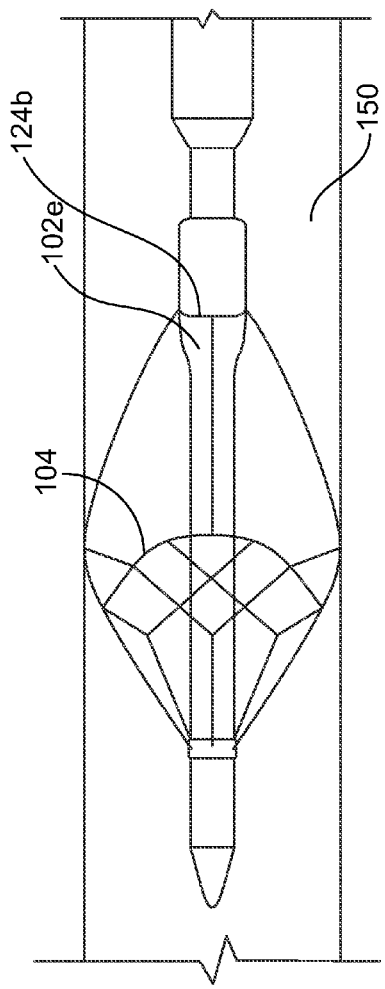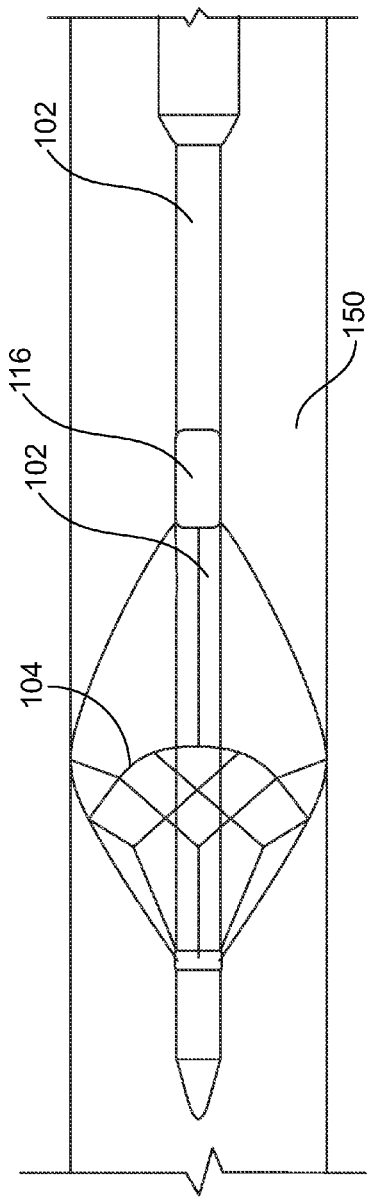

DETACHMENT MECHANISM FOR A CENTRAL VENOUS ACCESS FILTER AND METHOD OF USE

CROSS-REFERENCE TO RELATED APPLICATIONS

This application is a continuation of U.S. patent application Ser. No. 13/292,942, filed Nov. 9, 2011; and is related to U.S. patent application Ser. No. 11/849,225 filed Aug. 31, 2007 and U.S. patent application Ser. No. 12/684,839 filed Jan. 8, 2010, each of which are incorporated by reference.

BACKGROUND OF THE INVENTION

The accepted standard of care for patients with venous thromboembolism (VTE) is anticoagulant therapy. Inferior vena cava (IVC) filters are reserved for those patients who fail anticoagulant therapy, or have a complication or contraindication to anticoagulant therapy. Until the early 1970's, the only method of IVC interruption was surgical, either by clipping, ligation, or plication. The first clinical experience of an endoluminally-placed device to interrupt IVC flow was reported by Mobin-Uddin et al. in 1969. However, it was not until the introduction of a stainless steel umbrella-type filter by Greenfield et al. in 1973 that an effective method of endoluminally trapping emboli while simultaneously preserving IVC flow became possible. Indeed, for many years, the Greenfield filter set a benchmark by which newer filters were measured. Early generations of filters were inserted by surgical cut-down and venotomy. Eventually filters were able to be inserted percutaneously: initially through large 24 Fr sheaths, though newer generations of filters are able to be delivered through 6 Fr systems.

Despite the safety and efficacy of modern day filters, systemic anticoagulation remains the primary treatment for VTE. Either unfractionated or low molecular weight heparin followed by three months of oral anticoagulation in patients with proximal deep venous thrombosis (DVT) is approximately 94% effective in preventing pulmonary embolism (PE) or recurrent DVT. The routine placement of IVC filters in addition to anticoagulation in patients with documented DVT was investigated by Decousus et al. in a randomized trial. Decousus H, Leizorovicz A, Parent F, et al. A clinical trial of vena caval filters in the prevention of pulmonary embolism in patients with proximal deep-vein thrombosis. *N Engl J Med* 1998;338:409-415. This study revealed that the use of a permanent filter in addition to heparin therapy significantly decreased the occurrence of PE within the first 102 days compared to those without a filter. However, no effect was observed on either immediate or long-term mortality, and by 2 years, the initial benefit seen in the group of patients with filters was offset by a significant increase in the rate of recurrent DVT.

Despite the efficacy of anticoagulant therapy in the management of VTE, there are certain situations and conditions in which the benefits of anticoagulation are outweighed by the risks of instituting such a therapy. These include contraindications and complications of anticoagulant therapy. In such circumstances, there may be absolute or relative indications for filter insertion.

Currently, there are eight different types of permanent cava filters that are FDA approved. These include the Bird's Nest filter (Cook Incorporated, Bloomington, Ind.), Vena Tech LGM filter (B. Braun, Bethlehem Pa.), Vena Tech LP (B. Braun), Simon Nitinol filter (Bard, Covington, Ga.), Titanium Greenfield filter (Boston Scientific, Natick Mass.), Over-the-Wire Greenfield filter (Boston Scientific), TrapEase filter (Cordis Corp.) and the Gunther Tulip filter (Cook Inc.).

Well-founded concerns over the long-term complications of permanent IVC filters, particularly in younger patients in need of PE prophylaxis with a temporary contraindication to anticoagulation, has led to the development of temporary and retrievable filters. Temporary filters remain attached to an accessible transcutaneous catheter or wire. These have been used primarily in Europe for PE prophylaxis during thrombolytic therapy for DVT. Currently these devices are not approved for use in the United States. Retrievable filters are very similar in appearance to permanent filters, but with modifications to the caval attachment sites and/or hooks at one end that can facilitate their removal. Retrievable filters are currently available in the United States, examples of these include the Gunther Tulip (Cook Inc.), Opt Ease (Cordis Corp.), and Recovery nitinol filters (Bard Peripheral Vascular, Tempe, Ariz.) Lin P H, et al., *Vena caval filters in the treatment of acute DVT. Endovascular Today* 2005;Jan:40-50. The time limit of retrievability is in part dependent on the rate of endothelialization of the device, which typically occurs within 2 weeks. However, differences in design may extend the time period in which the filter may be safely retrieved.

Currently no consensus exists as to which patients have an indication for a retrievable filter. However, it is generally accepted that patients at high risk for pulmonary embolism or with documented PE and with a temporary contraindication to anticoagulation are candidates.

Certain circumstances preclude the placement of a filter in the infrarenal IVC. This includes thrombus extending into the infrarenal IVC, renal vein thrombosis or pregnancy. The safety of suprarenal placement of IVC filters is well documented, with no reported instances of renal dysfunction and no differences in the rates of filter migration, recurrent PE or caval thrombosis.

The rate of upper extremity DVT is on the rise. This is predominantly due to an increasing number of patients having short- and long-term upper extremity central venous access catheters. In one study, 88% of patients found to have an upper extremity DVT had a central venous catheter present at the site of thrombosis at the time of diagnosis or within the previous two weeks. Pulmonary embolism may complicate upper extremity DVT in a significant number of cases. In patients who have such a complication or contraindication to anticoagulation, a filter can be safely placed immediately below the confluence of the brachiocephalic veins. However, misplacement of an SVC filter is theoretically more likely than with an IVC filter because of the relatively short target area for deployment.

The most common imaging modality used for filter insertion is fluoroscopy, performed either in an interventional suite or an operating room. Bedside placement of filters has inherent advantages, particularly for critically ill patients in intensive care settings where transport can be avoided. Portable fluoroscopy, surface duplex ultrasound and intravascular ultrasound (IVUS) have all been used to assist with bedside filter placement.

CAVF placement frequently occurs concomitantly with central access line placement or in critically ill patients that already have a central access line in place. Heretofore, however, there have been few devices which combine the function of a central access catheter and a removable CAVF. Examples of a catheter coupled to a CAVF that is useful both as a central venous access catheter for administration of intravenous fluids, bioactive agents, contrast agents, flushing agents, pressurized fluids for mechanical thrombolysis and/or withdrawal of blood samples and for capture of thrombus or emboli are presented in U.S. patent application Ser. No. 11/849,225, filed Aug. 31, 2007, and U.S. patent application Ser. No. 12/684,839, filed Jan. 8, 2010, both of which are hereby incorporated in their entirety herein.

Regardless of the axial orientation of the CAVF, there may arise a need for longer term temporary placement and subsequent removal of the vena cava filter. Thus, it is advantageous to provide a detachment and retrieval mechanism which will permit the vena cava filter to be detached and retrieved on the CAVF. Such a convertible CAVF does not currently exist and would afford a practitioner flexibility in choice of placement of the CAVF without having to utilize multiple CAVF systems.

SUMMARY OF THE INVENTION

The present invention pertains generally to the field of vascular filters for capturing embolic material in the blood flow. More particularly, the present invention relates to a detachment mechanism for a vena cava filter disposed near the distal end of a central access catheter having a catheter body and a moveable outer sheath concentrically disposed over the catheter body. The assembly provides a central access venous filter ("CAVF") which may be delivered and deployed with a patient's vena cava to provide both central line access as well as embolic protection to the patient. The detachment mechanism of the present invention allows for detachment of the vena cava filter for longer term embolic protection needs and subsequent retrieval and removal using the same detachment mechanism as a retrieval mechanism in a second recovery procedure.

The present invention may be configured for either a femoral approach or a jugular approach to the inferior vena cava. CAVFs are typically deployed infrarenaly, but may also be deployed suprarenally. It will be understood that within the inferior vena cava blood flow is superior, i.e., toward the patients head. Thus, in all embodiments, the CAVF will be positioned so that it opens inferiorly, i.e., away from the patient's head and toward the direction of the blood flow. It will be appreciated, therefore, that in the present invention, the CAVF will have a different axial orientation on the central access catheter depending upon whether the device is intended for use in a femoral approach or a jugular approach.

In one aspect of the present invention, a detachment mechanism for a central venous access filter includes a catheter body and an outer sheath concentrically disposed about the catheter body. The outer sheath and the catheter body are moveable relative to one another. A filter member includes a first end coupled to the catheter body and a second end movable relative to the catheter body. The first end comprises a collar made of a shape memory material that is immovably coupled to the catheter body in a first state and movably coupled to the catheter body upon transition to a second state.

In another aspect of the present invention, a detachment mechanism for a central venous access filter includes a catheter body and an outer sheath concentrically disposed about the catheter body. The outer sheath and the catheter body are moveable relative to one another. A filter member includes a first end coupled to the catheter body and a second end movable relative to the catheter body. At least a section of the catheter body is comprised of shape memory material that is immovably coupled to the first end of the filter in a first state and movably coupled to the first end of the filter upon transition to a second state.

In a further aspect of the present invention, a detachment mechanism for a central venous access filter includes a catheter body and an outer sheath concentrically disposed about the catheter body. The outer sheath and the catheter body are moveable relative to one another. A filter member includes a first end coupled to the catheter body and a second end movable relative to the catheter body. The first end comprises a collar of shape memory material that is immovably coupled to the catheter body in a first state and movably coupled to the catheter body upon transition to a second state In yet another aspect of the present invention, a detachment mechanism for a central venous access filter includes a catheter body and an outer sheath concentrically disposed about the catheter body. The outer sheath and the catheter body are moveable relative to one another. A filter member includes a first end movably coupled to the catheter body and a second end movable relative to the catheter body. The catheter body comprises a region of shape memory material having a first expanded state and a second radially contracted state and the first end of the filter member comprises a collar of shape memory material having a first contracted state and a second expanded state. When the region of shape memory material and the first end are in their respective first states, the collar is inhibited from translating distally past the region of shape memory material, and when the region of shape memory material and the first end are in their respective second states, the collar can translate distally past the region of shape memory material.

In yet a further aspect of the present invention, a detachment mechanism for a central venous access filter includes a catheter body, and an outer sheath concentrically disposed about the catheter body. The outer sheath and the catheter body are moveable relative to one another. A filter member includes a first end movably coupled to the catheter body and a second end movable relative to the catheter body. At least a portion of the catheter body is comprised of shape memory material having a first expanded state and a second radially contracted state. The first end comprises a collar of shape memory material having a first contracted state and a second expanded state. When the shape memory portion of the catheter body and the collar are in their respective first states, the collar is immovably coupled to the catheter body, and when the catheter body and the collar are in their respective second states, the collar is movably coupled to the catheter body.

In a still further aspect of the present invention, a method of use for a detachment mechanism for a central venous access filter system is disclosed. The central venous access filter system includes a catheter body and an outer sheath concentrically disposed about the catheter body. The catheter body and the outer sheath are moveable relative to one another. A filter member includes a first end coupled to the catheter body via a shape memory detachment mechanism and a second end movable relative to the catheter body. The method comprises the steps of deploying the catheter filter within a blood vessel such that the filter member remains attached to the catheter body and has an enlarged diametric opening which opens facing a patient's blood flow and triggering a change of state of the shape memory detachment mechanism to release the filter member into the blood vessel.

These and other aspects and features of the present invention will be described in more detailed in the following more detailed description of the preferred embodiments of the invention taken with reference to the accompanying figures, in which like elements are identified by like reference numerals

BRIEF DESCRIPTION OF THE DRAWINGS

FIG. 8C illustrates the CAVF of FIG. 8B of the filter member being disposed within the lumen after the catheter body has been withdrawn from the lumen.

FIG. 8D illustrates the CAVF of FIG. 8C after the filter member has attached to the lumen wall.

FIG. 9C illustrates the CAVF of FIG. 9B after a portion of the catheter body has transitioned to immovably couple the CAVF to the catheter body.

FIG. 9D illustrates the CAVF of FIG. 9B after a collar of the CAVF has transitioned to immovably couple the CAVF to the catheter body.

DETAILED DESCRIPTION OF THE PREFERRED EMBODIMENTS

As used in this application, unless otherwise specifically stated, the terms "proximal" and "distal" are intended to refer to positions relative to the longitudinal axis of the catheter body 102. Those skilled in the art will understand that the catheter body 102 has a distal end which is first inserted into the patient and a proximal end which opposite the distal end. Additionally, the terms "inferior" or "inferiorly" are intended to refer to the anatomic orientation of being in a direction away from the patient's head while the terms "superior" or "superiorly" are intended to refer to the anatomic orientation of being toward the patient's head.

Figure 1:
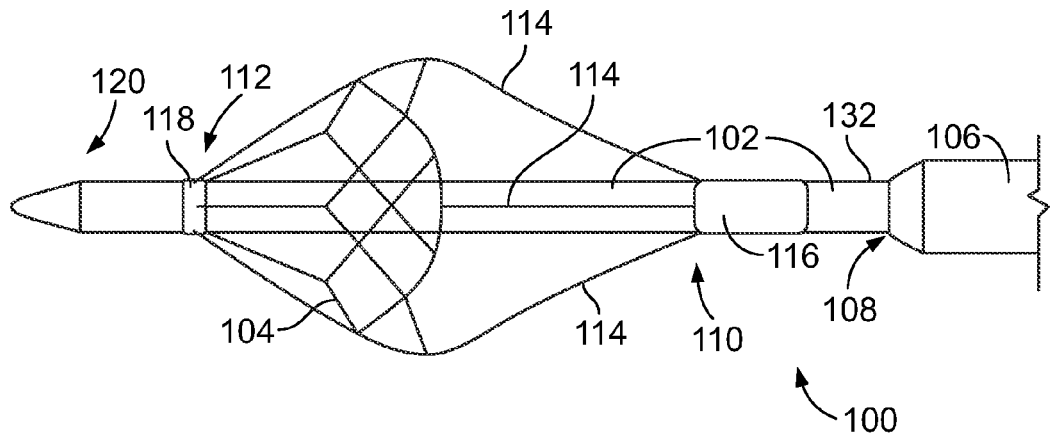
FIG. 1 is an illustration of an expanded CAVF attached to a catheter body.
Figure 2:
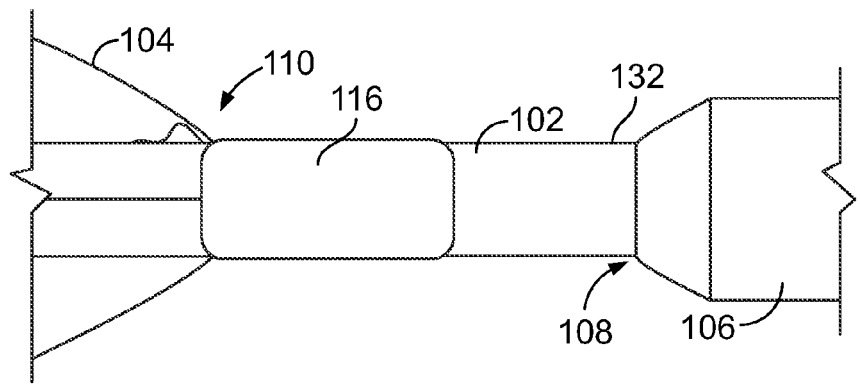
FIG. 2 is an enlarged view of a first end of the expanded CAVF of FIG. 1.

Referring to FIGS. 1 and 2, an exemplary central access vena cava filter catheter 100 is composed generally of a central venous access catheter body 102 and a filter member 104 disposed generally concentric relative to the catheter body 102. An outer sheath 106 is concentrically disposed over the catheter body 102 such that relative axial movement of the catheter body 102 and the outer sheath 106 either captures the filter member 104 within the outer sheath 106 or exposes the filter member 104.

The outer sheath 106 terminates in an annular opening 108 at a distal end thereof. The annular opening 108 is disposed between an inner surface of the outer sheath 106 and an outer surface 132 of the catheter body 102. One embodiment of the structure of the outer sheath 106 and the catheter body 102 and the relation therebetween that may be useful herein is described in U.S. patent application Ser, No. 13/083,053, filed Apr. 8, 2011, and hereby incorporated in its entirety herein.

A first end 110 of the filter member 104 may either be fixedly or movably attached to the catheter body 102. A second end 112 of the CAVF may be movably attached to the catheter body 102 or may be unattached and free to move in relation to the catheter body 102.

In one embodiment, a first collar member 116 is provided at the first end 110 of the filter member 104 that couples the filter member 104 to the catheter body 102. The first collar 116 may be concentrically engaged about the catheter body 102 at or adjacent the first end 110 of the filter member 104 and may be axially movable thereupon or fixedly attached thereto. In another embodiment, the first collar 116 is formed by connections between adjacent pairs of the longitudinal strut-like structural members 114 which circumscribe a circumference of the catheter body 102. Alternative configurations of the first collar 116 are contemplated by the present invention, including, for example, a helical winding, a closed tubular structure, and open tubular structure having a C-shaped transverse cross-section, or a plurality of longitudinally extending members coupling the filter member 104 to the catheter body 102

In a further embodiment, a second collar member 118 is provided at the second end 112 of the filter member 104 that couples the second end 112 of the filter member 104 to the catheter body 102. The second collar 118 may be concentrically engaged about the catheter body 102 and may be axially movable thereupon. In another embodiment, the second collar 118 is formed by connections between adjacent pairs of the longitudinal strut-like structural members 114 which circumscribe a circumference of the catheter body 102. Like the first collar 116, alternative configurations of the second collar 118 are contemplated by the present invention, including, for example, a helical winding, a closed tubular structure, and open tubular structure having a C-shaped transverse cross-section, or a plurality of longitudinally extending members coupling the filter member 104 to the catheter body 102

In one embodiment, the catheter body 102 has at least one disposed therethrough and is manufactured from a polymeric material, such as, for example, polytetrafluoroethylene (PTFE), ethylene tetrafluoroethylene (ETFE), fluorinated ethylene propylene (FEP), polyoxymethylene (POM, for example, as sold under the trademark DELRIN® available from DuPont), polybutylene terephthalate (PBT), polyether block ester, polyurethane, polypropylene (PP), polyvinyl-chloride (PVC), polyether-ester (for example, a polyether-ester elastomer as sold under the trademark ARNITEL® available from DSM Engineering Plastics), polyester (for example, a polyester elastomer as sold under the trademark HYTREL® available from DuPont), polyamide (for example, as sold under the trademark DURETHAN® available from Bayer or as sold under the trademark CRISTAMID® available from Elf Atochem), elastomeric polyamides, block polyamide/ethers, polyether block amide (PEBA, for example, as sold under the trade name PEBAX® available from Arkema, Inc.), silicones, polyethylene (PE), Marlex high-density polyethylene, Marlex low-density polyethylene, linear low density polyethylene, polyethylene terephthalate (PET), polyetheretherketone (PEEK), polyimide (PI), polyetherimide (PEI), polyphenylene sulfide (PPS), polyphenylene oxide (PPO), polysulfone, nylon, nylon-12 (as sold under the trademark GRILAMID® available from EMS American Grilon), perfluoro(propyl vinyl ether) (PFA), ethylene vinyl alcohol, polyolefin, polystyrene, epoxy, polyvinylidene chloride (PVdC), polycarbonates, ionomers, biocompatible polymers, other suitable materials, or mixtures, combinations, copolymers thereof, polymer/metal composites, and the like.

The strut-like structural members 114 of the filter member 104 are preferably fabricated of biocompatible materials, such as shape memory metal alloys, superelastic materials or elastic materials, including, without limitation, titanium, vanadium, aluminum, nickel, tantalum, zirconium, chromium, silver, gold, silicon, magnesium, niobium, scandium, platinum, cobalt, palladium, manganese, molybdenum and alloys thereof, such as zirconium-titanium-tantalum alloys, cobalt-chromium-molybdenum alloys, nitinol, and stainless steel. Alternatively, biocompatible polymers may be used to fabricate the strut-like structural members 114 of filter member 104.

Referring to FIG. 1, the filter member 104 may be configured to be a temporary filter member 104, meaning that the filter member 104 remains attached to the catheter body 102 and is removed from the patient with the catheter body 102. The filter member 104 may also be configured as a temporary filter member 104 that is convertible to a detachable and retrievable filter member 104. A mechanism for detachment of the filter member 104 from the catheter body 102 and a method for detaching the filter member 104 from the catheter body 102 are described by way of examples and not limitation hereinbelow.

The first collar 116 may be fabricated from shape memory materials, including shape memory metals and shape memory polymers ("SMM"). Alternatively, the first collar 116 may be fabricated from elastically deformable materials or plastically deformable materials. Regardless of whether the first collar 116 is made of SMM, elastically or plastically deformable materials, the first collar 116 has a first contracted state such that the first collar 116 is fixedly attached to the catheter body 102 and a second expanded state such that the first collar 116 is movable relative to the catheter body 102.

Referring to FIG. 1, a configuration where the first collar 116 is fixed to the catheter body 102 and the second collar 118 is movably attached to the catheter body 102, for example, movably attached to the catheter body 102, and allows the filter member 104 to move axially in accommodation of radial expansion and contraction of the filter member 104. In this first state of the first collar 116, the filter member 104 is a temporary filter member 104, being fixedly held on the catheter body 102 by the first collar 116. It will be understood that when the first collar 116 is in its first state, it is compressing against the filter member 104 and catheter body 102 and is retained by a friction fit due to this compressive force.

Figure 3A:
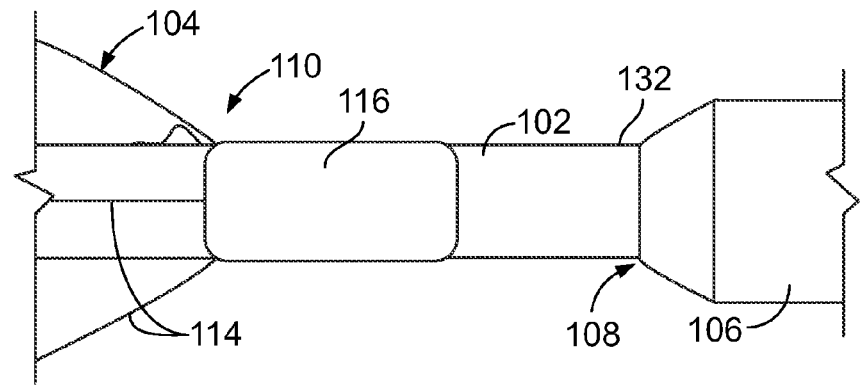
FIG. 3A illustrates an embodiment of a CAVF detachment mechanism in a first state.
Figure 3B:
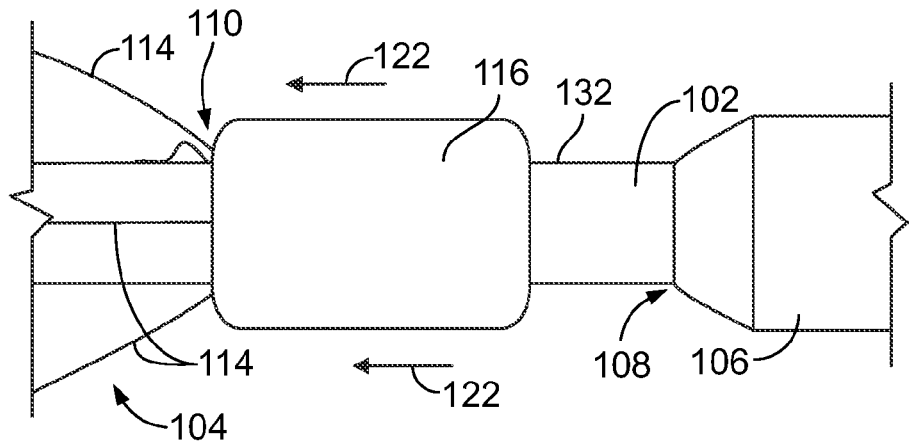
FIG. 3B illustrates the detachment mechanism of FIG. 3A in a second state.

When the first collar 116 transitions to its expanded state, as depicted in FIG. 3B, the first collar 116 expands, releasing the compressive force and releasing the filter member 104 from the catheter body 102. FIG. 3B illustrates the first collar 116 in a second expanded state where the first collar 116 has expanded to a size larger in diameter than the catheter body 102 to become movably attached to the catheter body 102. In the second expanded state, the first collar 116 is free to slide distally toward a distal end 120 (See FIG. 1) of the catheter body 102, as illustrated by arrows 122. Thus, in the second extended state, the first collar 116 is free to slide off the catheter body 102 such that the temporary filter member 104 converts to a detachable filter member 104 for placement in a blood vessel.

Figure 4A:
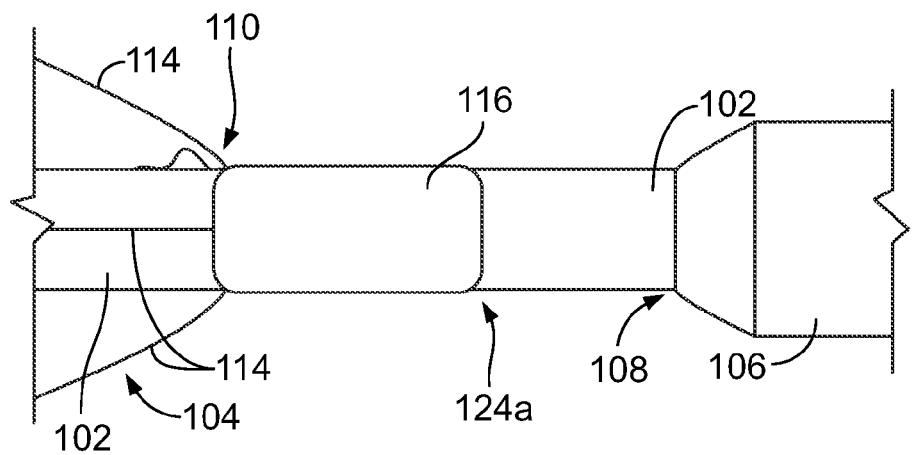
FIG. 4A illustrates another embodiment of a CAVF detachment mechanism in a first state.
Figure 4B:
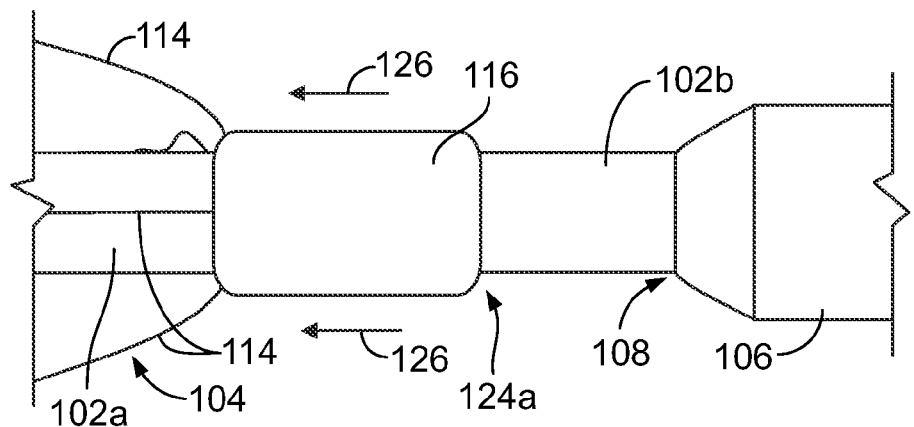
FIG. 4B illustrates the detachment mechanism of FIG. 4A in a second state.
Figure 4C:
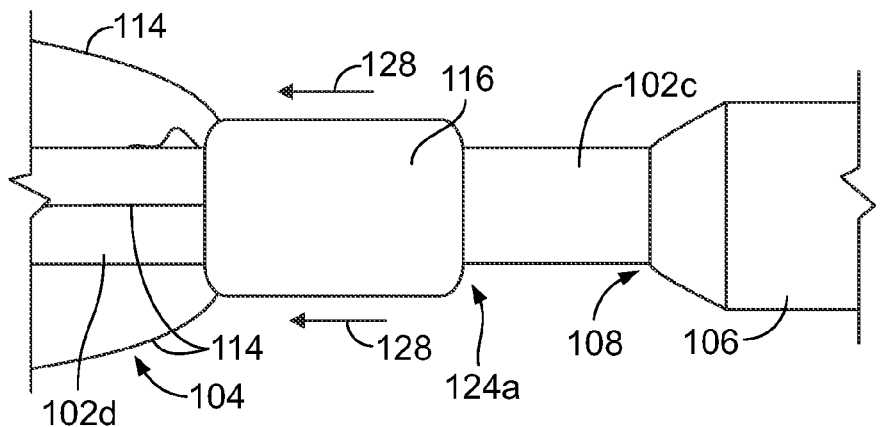
FIG. 4C illustrates another embodiment of the detachment mechanism of FIG. 4A in a second state.

In another embodiment, as illustrated in FIGS. 4A-4C, the collar 116 may be fabricated from SMM, elastically or plastically deformable materials, as illustrated in the prior embodiment described with regard to FIGS. 3A and 3B. In this embodiment, at least a portion 102a of the catheter body 102 distal to a proximal side 124a of the first collar 116 is manufactured from SMM. FIG. 4A illustrates the portion 102a of the catheter body 102 in a first state where the portion 102a is diametrically expanded so as to be fixedly attached to the first collar 116.

FIG. 4B illustrates the portion 102a of the catheter body 102 in a second state such that the portion 102a is smaller in diameter than a remaining portion 102b of the catheter body 102. In the second state, the portion 102a has contracted so that the first collar 116 is movably attached to the portion 102a such that the first collar 116 is free to slide distally toward the distal end 120 (See FIG. 1) of the catheter body 102, as illustrated by arrows 126. Thus, in the second state of the portion 102a, the first collar 116 is free to slide off the catheter body 102 such that the temporary filter member 104 converts to a detachable filter member 104 for placement in a blood vessel.

It is contemplated that for ease of manufacture or other reasons that a larger portion, a majority, or all of the catheter body 102 may be manufactured from SMM. For example, FIG. 4C illustrates an embodiment where portions 102c and 102d of the catheter body that are disposed proximally and distally, respectfully, of the proximal side 124a of first collar 116 are both made from SMM. In this embodiment, in the first state of the portions 102c, 102d, the first collar 116 is fixedly attached to the catheter body 102 as illustrated in FIG. 4A. In the second state of the portions 102c, 102d, the first collar 116 is free to slide distally off the catheter body 102 as indicated by arrows 128.

Figure 5A:
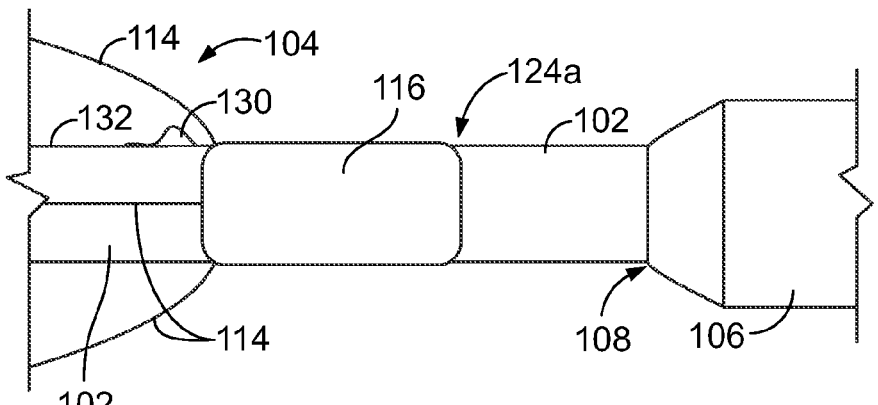
FIG. 5A illustrates an embodiment of a CAVF detachment mechanism in a first state.
Figure 5B:
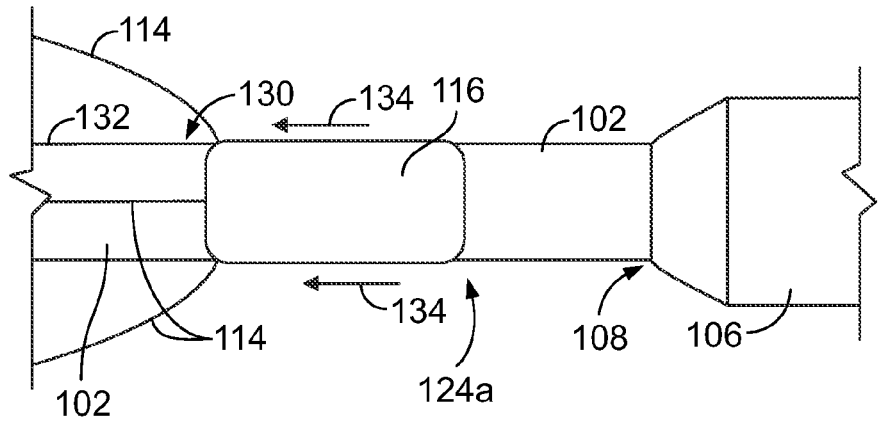
FIG. 5B illustrates the detachment mechanism of FIG. 5A in a second state.
Figure 5C:
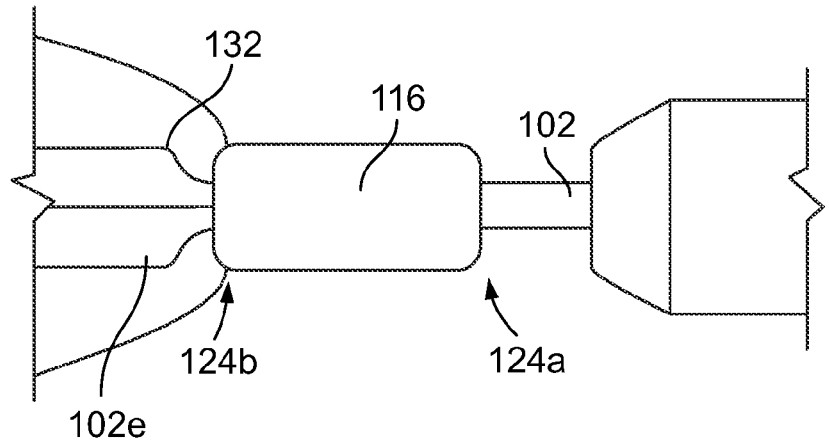
FIG. 5C illustrates an alternative embodiment of a CAVF detachment mechanism in a first state.
Figure 5D:
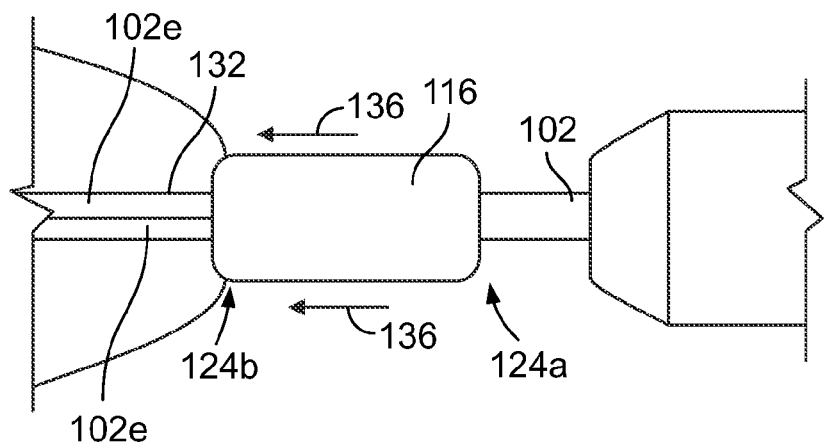
FIG. 5D illustrates the detachment mechanism of FIG. 5C in a second state.

In a further embodiment, as illustrated in FIGS. 5A and 5B, the catheter body 102 or a portion of the catheter body 102 may or may not be made of SMM as illustrated in the prior embodiment described with regard to FIGS. 4A-4C. In this embodiment, the first collar 116 is made of a material having a fixed shape and is movably attached to the catheter body 102. Referring to FIG. 5A, the catheter body 102 comprises a region 130 of SMM disposed on a distal side of the first collar 116 and having a first radially expanded state. In the first radially expanded state, the region 130 protrudes from the outer surface 132 of the catheter body 102. The protruding region 130 inhibits the first collar 116 from translating distally past the region 130. In a second state, the region 130 is contracted into the surface 132 such that the first collar 116 is free to slide distally past the first region 130 and off the catheter body 102 as indicated by arrows 134. In another embodiment, as illustrated in FIGS. 5C and 5D, at least a portion 102e of the catheter body 102 distal to a distal side 124b of the first collar 116 is manufactured from SMM. FIG. 5C illustrates the portion 102e in a first state where the portion 102e is diametrically expanded so as to be larger in diameter than at least an inner diameter of the first collar 116. Thus, the portion 102e in the first state inhibits the first collar 116 from translating distally past the portion 102e. In a second state, the portion 102e is diametrically contracted so as to be smaller in diameter than at least an inner diameter of the first collar 116 such that the first collar 116 is free to slide distally past the portion 102e and off the catheter body 102 as indicated by arrows 136.

Figure 6A:
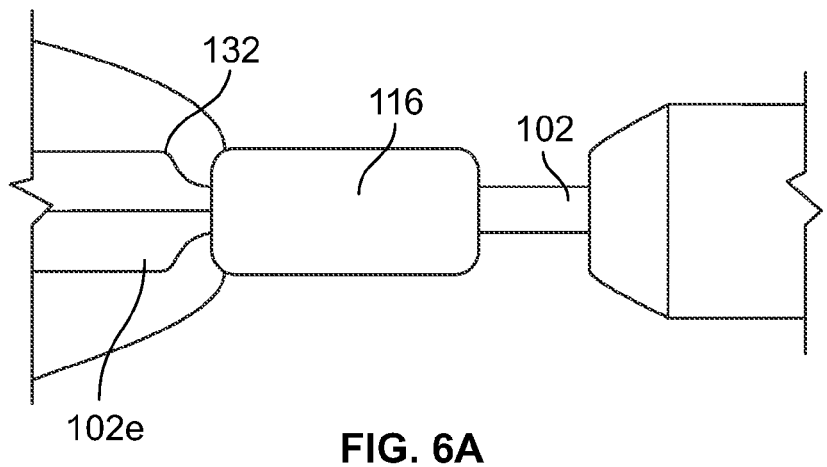
FIG. 6A illustrates an embodiment of a CAVF detachment mechanism in a first state.

In further embodiments, one or more portions, for example, the portions 102a-102e of the catheter body 102, one or more regions, for example, the region 130, and/or the first collar 116 may be made from SMM. For example, in one embodiment, the first collar 116 and the portion 102e of the catheter body 102 are both made of SMM. As illustrated in FIG. 6A, the portion 102e is in a diametrically expanded first state, such that the outer surface 132 is larger in diameter than at least an inner diameter of the first collar 116, which is also illustrated in a first state. When the first collar 116 and the portion 102e are in their first states, the first collar 116 is inhibited from translating distally past the diametrically expanded portion 102e. In addition, in the first state, the first collar 116 may be fixedly or movably attached to the catheter body 102.

Figure 6B:
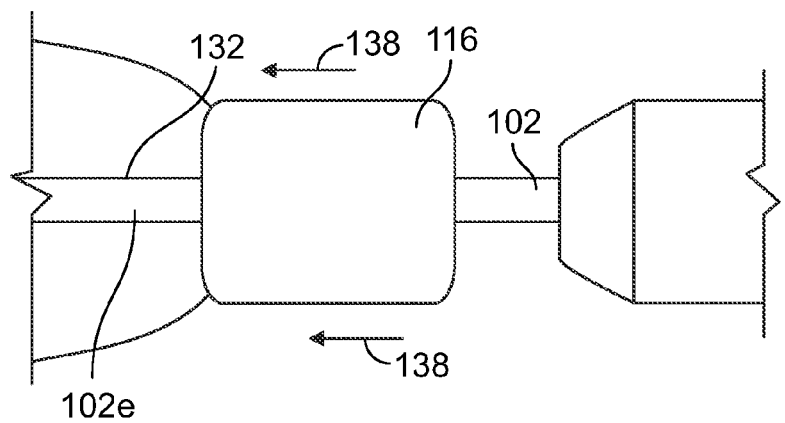
FIG. 6B illustrates the detachment mechanism of FIG. 6A in a second state.

FIG. 6B illustrates the embodiment of FIG. 6A when the first collar 116 and portion 102e of the catheter body 102 are in their respective second states. The first collar 116 has a second state that is diametrically expanded relative to its first state. The protrusion 102e has a second state that is diametrically contracted relative to its first state. Thus, when the portion 102e and the first collar 116 are in their second states, the first collar 116 can freely translate distally past the portion 102e and off the distal end 120 of the catheter body 102 as indicated by arrows 138.

Figure 7A:
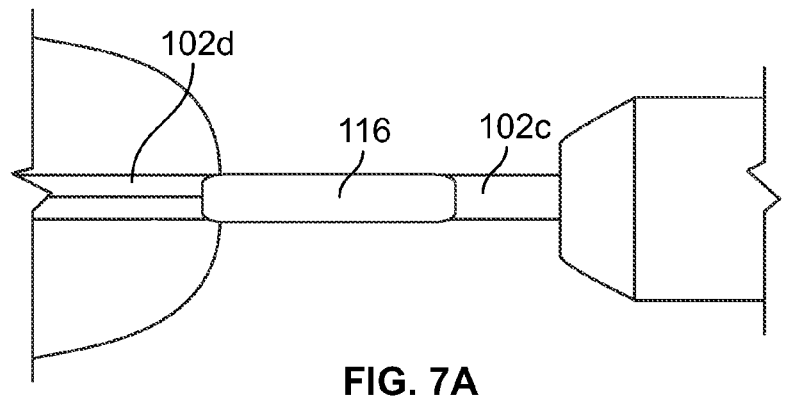
FIG. 7A illustrates an embodiment of a CAVF detachment mechanism in a first state.
Figure 7B:
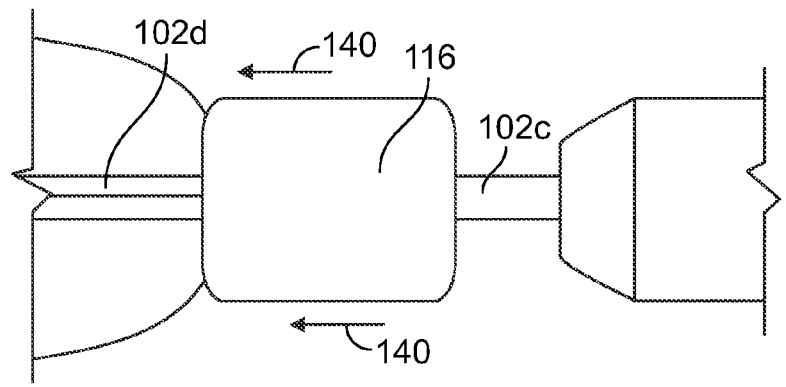
FIG. 7B illustrates the detachment mechanism of FIG. 7A in a second state.

In a further embodiment, as illustrated in FIGS. 7A and 7B, the portions 102c and 102d of the catheter body 102 and the first collar 116 are made of SMM. FIG. 7A illustrates the portions 102c, 102d in a diametrically expanded first state and the first collar 116 in a diametrically contracted first state. When the first collar 116 and the portions 102c, 102d are in their first states, the first collar 116 is fixedly attached to the portion 102d.

FIG. 7B illustrates the embodiment of FIG. 7A when the first collar 116 and the portions 102c, 102d are in their respective second states. The first collar 116 has a second state that is diametrically expanded relative to its first state. The portion 102d has a second state that is diametrically contracted relative to its first state. Thus, when the first collar 116 and the portion 102d are in their second states, the first collar 116 can freely translate distally past the portion 102e and off the distal end 120 of the catheter body 102 as indicated by arrows 140.

Figure 8A:
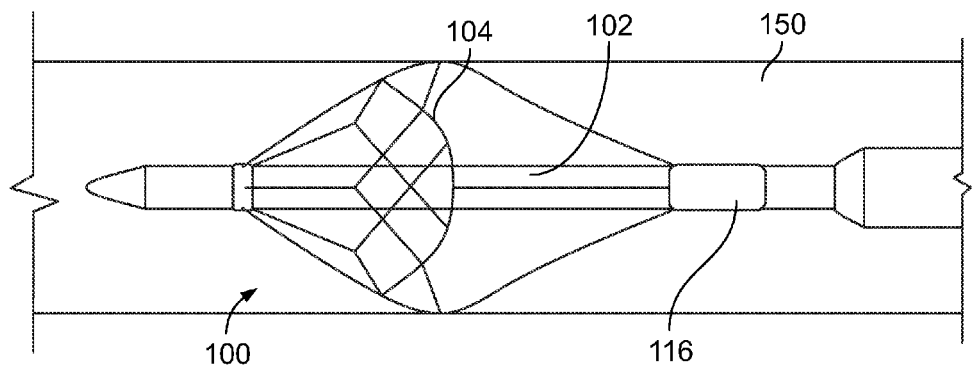
FIG. 8A illustrates an embodiment of a CAVF disposed within a lumen.
Figure 8B:
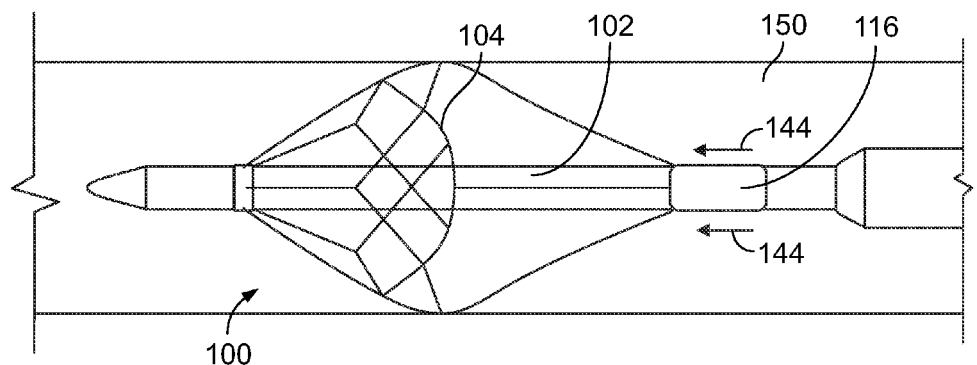
FIG. 8B illustrates the CAVF of FIG. 8A after the filter member has detached from the catheter body.

FIGS. 8A-8D depict an example of the delivery of the filter member 104 into a lumen 150. FIG. 8A shows the central venous access catheter 100 disposed within the lumen 150. This depiction employs the embodiment of the invention as shown in FIGS. 3A-3B, with the first collar 116 being in its first contracted state. It should be understood that any embodiment of the invention, including those shown in FIGS. 3A, 4A, 5A, 6A, and 7A, are included in this example of the delivery of the filter member 104. Upon entry to the lumen 150 the central venous access catheter 100 is advanced to a desired position within the lumen 150 for delivering the filter member 104. As illustrated in FIG. 8B, when the central venous access catheter 100 is advanced to the desired location in the lumen 150, the first collar 116 can be transitioned to its second state, whereupon the catheter body 102 may be retracted from the filter member 104, as indicated by arrows 144.

As illustrated in FIG. 8C, when the first collar 116 has been transitioned to its second state, the filter member 104 can move distally along the catheter body 102 until both the second collar 118 and the first collar 116 move distally off the distal end 120 of the catheter body 102. FIG. 8D shows the detached filter member 104 delivered to the desired location within the lumen 150 after the central venous access catheter 100 has been removed from the lumen 150. Upon delivery to the desired location in the lumen 150, the filter member 104 may anchor against the vessel wall by virtue of the radial force of the deployed filter acting against the vessel lumen wall 152, or, alternatively, the filter may be attached to the lumen wall 152 via anchoring members 154 attached to the strut-like members 114 of the filter member 104. This attachment will prevent the filter member 104 from migrating from the desired delivery location within the lumen 150. Anchoring members 154 may, by way of example and not limitation, include a variety of forms, including hooks, barbs, rails, feet, prongs, as well as other types of anchoring members.

Figure 9A:
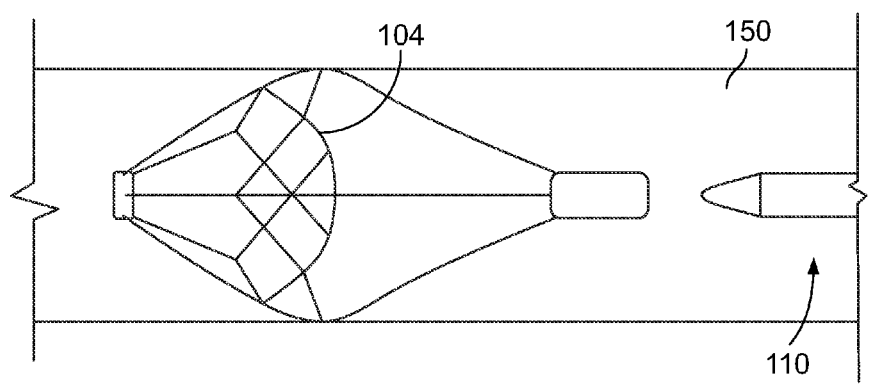
FIG. 9A illustrates an embodiment of a CAVF having been previously detached from the catheter body, now about to be retrieved.
Figure 9B:
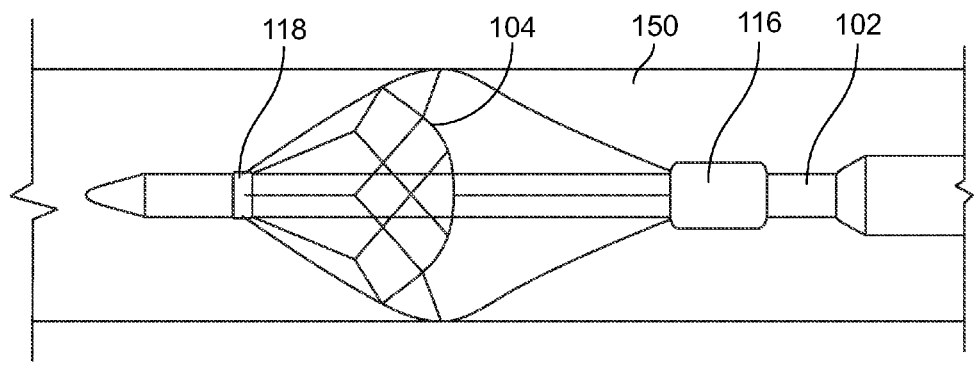
FIG. 9B illustrates the CAVF of FIG. 9A after the catheter body has been advanced through the collars of the CAVF.

Once delivered, the filter member 104 can remain in the lumen 150 indefinitely or until a removal indication presents. When the removal of the filter member 104 is desired, a central venous access catheter 100 can be introduced into the lumen 150 and the filter member 104 retrieved. Examples of this procedure are illustrated in FIGS. 9A-9D. FIG. 9A shows the central venous access catheter 100 after being introduced into the lumen 150 and advanced to the location of the filter member 104. FIG. 9B shows the catheter body 102 after being advanced through the first collar 116 and the second collar 118 such that each collar circumscribes the circumference of the catheter body 102. As illustrated in FIG. 9C, the portion 102e of the catheter body 102 distal a distal side 124b of the first collar 116 is transitioned from a first contracted state to a second expanded state. In the second state, the portion 102e constrains the first collar 116, inhibiting the first collar 116 from moving distal the portion 102e. The portion 102e may now be translated relative to the outer sheath 106 to draw the filter member 104 into the outer sheath 106 and thereby collapse the filter member 104. Subsequent to securing the collapsed filter member 104 within the outer sheath 106, the filter member 104 can be withdrawn from the lumen 150 with the outer sheath 106.

It should be understood that any of the foregoing described embodiments of the invention may be used for retrieval of the filter member 104. For example, as shown in FIG. 9D, instead of the portion 102e of the catheter body 102 comprising SMM, the first collar 116 could comprise SMM. In that embodiment, the first collar 116 is movably coupled to the catheter body 102 in a first expanded state and immovably coupled to the catheter body 102 in a second contracted state. FIG. 9D depicts the first collar 116 in its second contracted state, thus immovably coupled to the catheter body 102. Once the filter member 104 is thus affixed to the catheter body 102, the filter member 104 can be collapsed into the outer sheath 106 and withdrawn from the lumen 150 therewith.

Furthermore, it is contemplated that the method of retrieval of the filter member 104 may be different from the method of detachment used in delivering the filter member 104. For example, the first collar 116 of the filter member 104 could be expanded to allow the filter member 104 to detach from the catheter body 102 for delivery of the filter member 104, as depicted in FIGS. 8A-8D, and the portion 102e of the catheter body 102 could be expanded to couple the filter member 104 to the catheter body 102 to retrieve the filter member 104, as depicted in FIG. 9C.

Figure 10A:
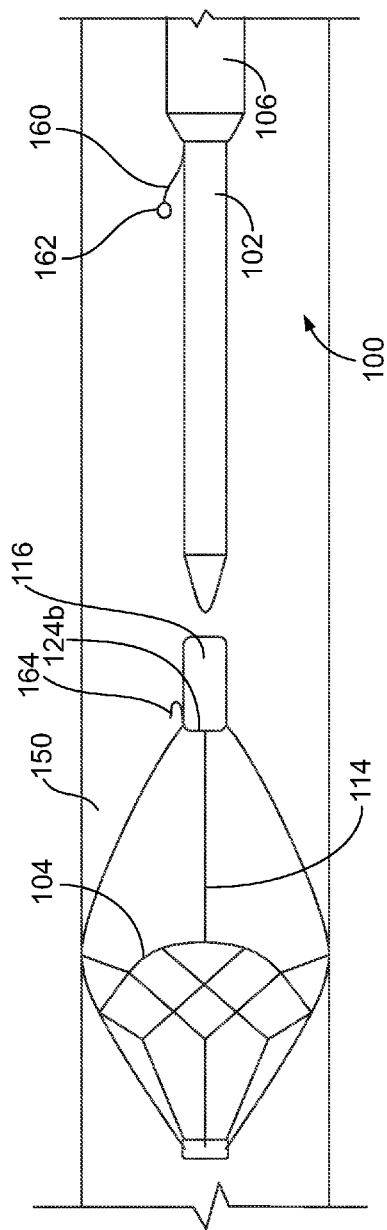
FIG. 10A illustrates an embodiment of a CAVF including a snare and a hook as a mechanical fixture for the retrieval of the CAVF.
Figure 10B:
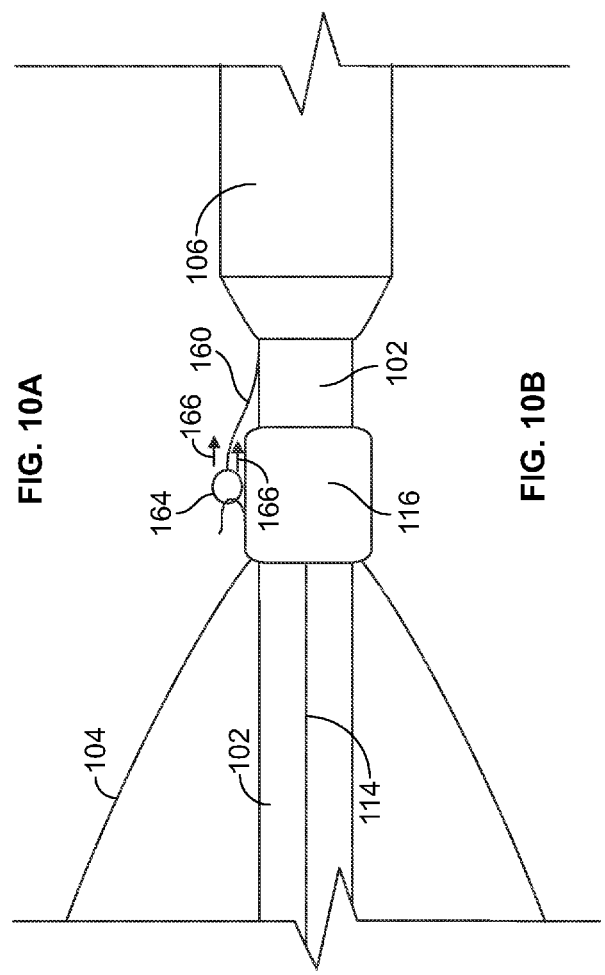
FIG. 10B is a view of the CAVF of FIG. 9A after the hook and the snare have engaged.

In another embodiment, as illustrated in FIGS. 10A and 10B, the filter member 104 may be retrieved using a mechanical fixture 160. In the example depicted in FIG. 10A, the mechanical fixture 160 includes a snare 162 and is attached to the catheter body 102. The snare 162 has a corresponding hook 164 attached, for example, to the distal end 124b of the first collar 116. The locations of the mechanical fixture 160 and the hook 164 are exemplary and can be located elsewhere on the central venous access catheter 100 and filter member 104, respectively. As depicted in FIG. 10B, as the catheter body 102 advances through the filter member 104, the snare 162 will engage with the hook 164. Once engaged, the snare 162 can exert a force on the hook 164 in the direction of arrows 166, thereby collapsing and drawing the filter member 104 into the outer sheath 106 for subsequent removal from the lumen 150. The mechanical fixture 160 is exemplary and does not limit the scope of devices that can be used for retrieving the CAVF 104. Other such fixtures, by way of example and not limitation, may include cooperating engaging members, such as threads, slots, projections, detents, or the like.

All of the hereinabove embodiments of a filter member 104 detachment mechanism may be operated via the same methodology to release the filter member 104 as described. The SMM may respond to a variety of different stimulus by transitioning between the first and second states. Such stimulus triggers include by way of example and not limitation, changes in light, changes in temperature, changes in chemical composition of the environment, application of electrical current, and other changes.

While the present invention is not limited to specific dimensional sizes of either the catheter body member 102 or the outer sheath 106, an exemplary outer diameter size of the outer sheath 106 is between 7 Fr (2.3 mm) and 9 Fr (3.0 mm), while an exemplary outer diameter size of the catheter body 102 is between 6 Fr (2.0 mm) and 8 Fr (2.7 mm).

It will be appreciated by those skilled in the art that changes may be made to the embodiments described hereinabove without departing from the broad concepts disclosed therein. It is understood, therefore, that this disclosure is not limited to the particular embodiments disclosed, but it is intended to cover modifications that may include a combination of features illustrated in one or more embodiments with features illustrated in any other embodiments. For example, any of the structures including SMM, elastically deformable or plastically deformable materials, and having first and second diametric states, as described hereinabove, may be used in detachment and/or retrieval of the filter member 104. Accordingly, this description is to be construed as illustrative only and is presented for the purpose of enabling those skilled in the art to make and use the detachment mechanisms described herein and to teach the best mode of carrying out the same.

There has been described a detachment mechanism for a filter member 104 for delivering the filter member 104 to a desired location within a lumen 150 of a blood vessel. The detachment mechanism comprises a SMM that transitions between states in response to stimulus. The detachment mechanism allows the filter member 104 to be deployed temporarily in the vessel while remaining attached to a catheter body 102. Alternatively, or in addition, the detachment mechanism also allows the filter member 104 be detached from the catheter body 102 at a desired position with the lumen 150 and subsequently retrieved from the lumen 150 in a later procedure. These and other aspects of the present invention are provided by way of non-limiting examples, with the claims appended hereto serving to define the scope of the subject matter regarded as the invention

What is claimed is:

1. A method of use for a detachment mechanism for a central venous access filter system having a catheter body, an outer sheath concentrically disposed about the catheter body wherein the catheter body and the outer sheath are moveable relative to one another, and a filter member having a first end coupled to the catheter body via a shape memory detachment mechanism and a second end movable relative to the catheter body, the shape memory detachment mechanism having a first state that immovably couples the first end of the filter member to the catheter body and a second state that removably couples the first end of the filter member to the catheter body, the method comprising the steps of:
   a. deploying the filter member within a blood vessel such that the filter member remains attached to the catheter body and has an enlarged diametric opening which opens facing a patient's blood flow and capturing embolic material within the opened filter member; and
   b. triggering a change of state of the shape memory detachment mechanism from its first state to its second state thereby releasing the filter member from the catheter body.

2. The method according to claim 1, further comprising the step of withdrawing the catheter body and the outer sheath from the blood vessel.

3. The method according to claim 1, further comprising the step of introducing a mechanical fixture into the blood vessel to retrieve the filter member.

4. The method according to claim 1, further comprising the steps of introducing the catheter body and the outer sheath into the blood vessel, wherein the outer sheath includes a mechanical fixture attached to the distal end of the outer sheath and retrieving the filter with the mechanical fixture.

5. The method according to claim 1, wherein at least a portion of the catheter body comprises shape memory material that can be movably coupled to the filter member in a first state and immovably coupled to the filter member in a second state, further comprising the steps of:
   a. introducing the catheter body and the outer sheath into the blood vessel;
   b. disposing the catheter body such that at least one of the first end and the second end circumscribe the circumference of the catheter body; and
   c. triggering a change of state in the shape memory material of the catheter body.

6. The method according to claim 1, wherein the triggering the change of state comprises applying an electrical or thermal energy to the shape memory detachment mechanism.

7. The method according to claim 1, wherein the shape memory detachment mechanism further comprises a collar member at the first end of the filter member.

8. The method according to claim 7, further comprising the step of coupling the collar member to the catheter body.

* * * * *